United States Patent
Kahn et al.

(10) Patent No.: US 10,842,968 B1
(45) Date of Patent: Nov. 24, 2020

(54) USING LOCAL DATA TO IMPROVE SLEEP EXPERIENCE

(71) Applicants: Philippe Richard Kahn, Santa Cruz, CA (US); Arthur Kinsolving, Santa Cruz, CA (US)

(72) Inventors: Philippe Richard Kahn, Santa Cruz, CA (US); Arthur Kinsolving, Santa Cruz, CA (US)

(73) Assignee: DP Technologies, Inc., Scotts Valley, CA (US)

(*) Notice: Subject to any disclaimer, the term of this patent is extended or adjusted under 35 U.S.C. 154(b) by 90 days.

(21) Appl. No.: 14/332,288

(22) Filed: Jul. 15, 2014

Related U.S. Application Data (60) Provisional application No. 61/846,582, filed on Jul. 15, 2013.

(51) Int. Cl.
*A61M 21/02* (2006.01)
*A61M 21/00* (2006.01)

(52) U.S. Cl.
CPC ..... *A61M 21/02* (2013.01); *A61M 2021/0016* (2013.01); *A61M 2021/0027* (2013.01); *A61M 2021/0044* (2013.01); *A61M 2021/0066* (2013.01); *A61M 2021/0083* (2013.01)

(58) Field of Classification Search
CPC ...... A61M 21/00–02; A61M 2021/0005–0028
USPC ...................................................... 600/26–28
See application file for complete search history.

(56) References Cited

U.S. PATENT DOCUMENTS

| | | | |
|---|---|---|---|
| 3,712,292 A * | 1/1973 | Zentmeyer, Jr. | A61M 21/00 600/28 |
| 6,028,514 A | 2/2000 | Lemelson et al. | |
| 6,031,455 A | 2/2000 | Grube et al. | |
| 6,608,559 B1 | 8/2003 | Lemelson et al. | |
| 7,705,723 B2 | 4/2010 | Kahn et al. | |
| 8,523,758 B1 * | 9/2013 | Kirby | A61M 21/02 600/26 |
| 2005/0143617 A1 * | 6/2005 | Auphan | A61B 5/08 600/26 |
| 2006/0036619 A1 | 2/2006 | Fuerst et al. | |
| 2006/0106275 A1 * | 5/2006 | Raniere | A61M 21/02 600/26 |
| 2008/0238659 A1 | 10/2008 | Houde et al. | |
| 2009/0204434 A1 | 8/2009 | Breazeale, Jr. | |
| 2009/0319180 A1 | 12/2009 | Robinson et al. | |
| 2010/0009811 A1 * | 1/2010 | Lee | A63B 24/0084 482/8 |
| 2010/0117838 A1 | 5/2010 | Humbard | |

(Continued)

OTHER PUBLICATIONS

Baskas, Harriet. "How to get a quiet hotel room", Dec. 11, 2008. Accessed Sep. 19, 2018 http://www.nbcnews.com/id/28161148/ns/travel-business_travel/t/do-not-disturb-how-get-quiet-hotel-room/#.W6OWKDbruck (Year: 2008).*

*Primary Examiner* — Catherine B Kuhlman
(74) *Attorney, Agent, or Firm* — Nicholson De Vos Webster & Elliot LLP; Judith Szepesi (57) ABSTRACT

A method and apparatus comprising to utilize local data to improve sleep is described. The method includes identifying local data relevant to a user's sleep quality, evaluating a user's sleep environment and sleep settings, and changing the user's sleep environment and/or sleep settings based on the local data.

21 Claims, 8 Drawing Sheets

(56) References Cited

U.S. PATENT DOCUMENTS

2011/0224510 A1* 9/2011 Oakhill .................. A61B 5/11
600/301

* cited by examiner

Exemplary Types of Local Data

- Locality Specific Data (permanent data associated with locality)
    - Sunrise/Sunset time
    - Length of night
    - Phases of the moon
    - Proximity to pollution
        - Light pollution: city, highly-lit area
        - Noise pollution: airport, freeway, train station, train tracks, large streets, factory
            - Positive noise pollution: ocean, rain forest
        - Air pollution: factor, refinery, dump
        - Other pollution: electrical or magnetic fields, infrasounds, ultrasounds, etc.
            - nuclear plant, high voltage transmission lines, electrical plant, certain factories.
    - Allergens
- Local Conditions
    - Current allergen load
    - Current temperature, atmospheric pressure, air quality, pollution
    - Current traffic levels
    - Current events that may impact local conditions
        - Fires, explosions, toxic spills, fireworks

USING LOCAL DATA TO IMPROVE SLEEP EXPERIENCE

RELATED APPLICATIONS

The present application claims priority to U.S. Provisional Application No. 61/846,582, filed on Jul. 15, 2013, which is incorporated herein by reference.

FIELD

The present invention relates to sleep, and more particularly to using local data to improve sleep quality.

BACKGROUND

It is well known that the quality of sleep impacts people's health significantly. There are a number of sleep tracking applications, that allow a user to track sleep, using accelerometers.

Many factors can impact sleep. For example, if a space is too bright, in general sleep quality will be degraded. Similarly, it is difficult to have restful sleep in a very loud environment.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

A system that enhances a user's sleep experience by using local data is described. The local data may be locality specific data, such as sunrise/sunset time at the current location, the length of the night, phase of the moon, visibility of the moon, noise levels, light levels, pollution, or long-term allergens. The local data may further be current environmental conditions in the locality, such as current allergen load, current temperature, barometric pressure, air quality, pollution levels, current traffic levels, and/or other current events or occurrences that have impact on local conditions (forest fires, toxic spills, etc.) By taking this local data into account when making recommendations for the user, the user's sleep experience is improved. In one embodiment, locality information used to obtain local data is obtained based on a GPS, cellular network triangulation, or wireless mapping-based location determination. The local data may be obtained from various third party sources, and/or a server that aggregates third party sources. These third party sources may be government sources, private sources, and/or directly obtained data using sensor information obtained from local user devices or sensors.

In one embodiment, the system may automatically adjust the user's sleep environment, may alert the user to adjust his or her sleep environment manually. In addition to adjusting the environment, the system may further prompt the user to go to sleep at a different time, or shift the user's wake-up alarm time based on this data.

In one embodiment, the system collects sleep data from users. This may provide data for the system, to alter recommendations based on measured results. In one embodiment, the system uses the sleep data from many users to generate cumulative sleep data, which is used, in one embodiment, for cumulative data analysis. In one embodiment, users may opt into, or opt out of, providing their data for the cumulative data analysis. This cumulative data analysis may result in better initial recommendations and settings. In one embodiment, the system may also be able to provide data regarding pollution effects, noise impact analysis, and similar data to relevant entities, such as governments, regulatory agencies, etc.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional and other changes may be made without departing from the scope of the present invention. The following detailed description is, therefore, not to be taken in a limiting sense, and the scope of the present invention is defined only by the appended claims.

Figure 1:
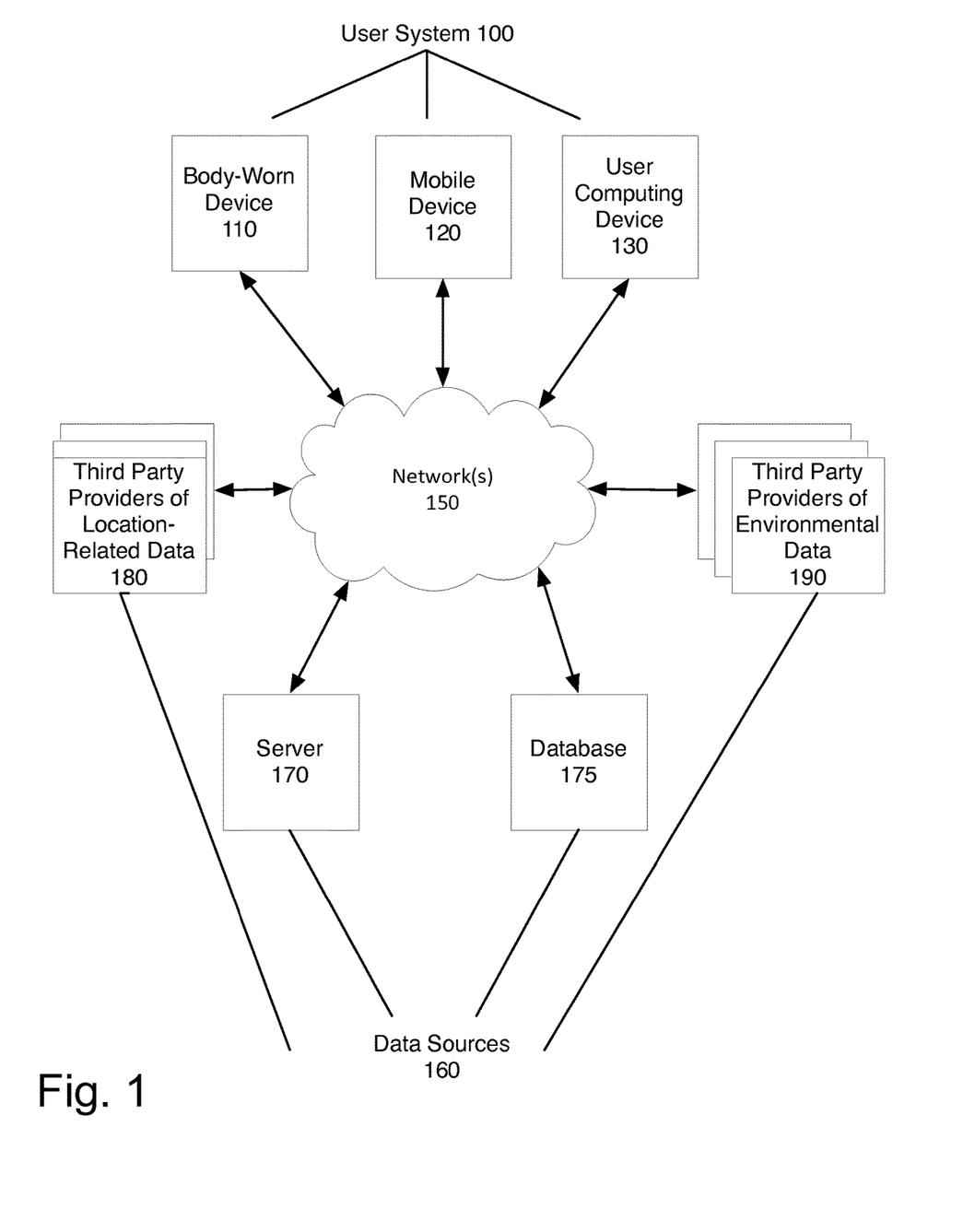
FIG. 1 is one embodiment of a network environment that may be used with the present invention.

FIG. 1 is one embodiment of a network environment that may be used with the present invention. The system includes a user system 100 which may include one or more of body-worn device 110, user mobile device 120, and computing device 130. The user system 100 includes one or more sensors. The sensors are used to track the user's sleep. In one embodiment, the sensors are also used to determine local data. In one embodiment, the user system 100 includes a communication mechanism to receive local data from one or more data sources 160. The data sources 160, accessed through network 150 may include third party providers of location related data 180, third party providers of environmental data 190, server 170, and/or a database 175, which collects such data.

The user system 100 utilizes a plurality of sensors to capture user data, and optionally local data. In one embodiment, the system optimizes a user's sleep environment, sleep experience, and alarm timing based on local data and user sleep data. In one embodiment, sleep analysis is done on server 160, or the user's mobile device 120 and/or computing device 130.

The server 160 in one embodiment collects data from a large number of users, to perform statistical analysis. In one embodiment, the system correlates local data with the collected local data. In one embodiment, sleep data and local data correlations, as determined by the server 160 may be used to create customized recommendations for users, and adjust the sleep environment, sleep experience, and/or alarm timing.

Figure 2:
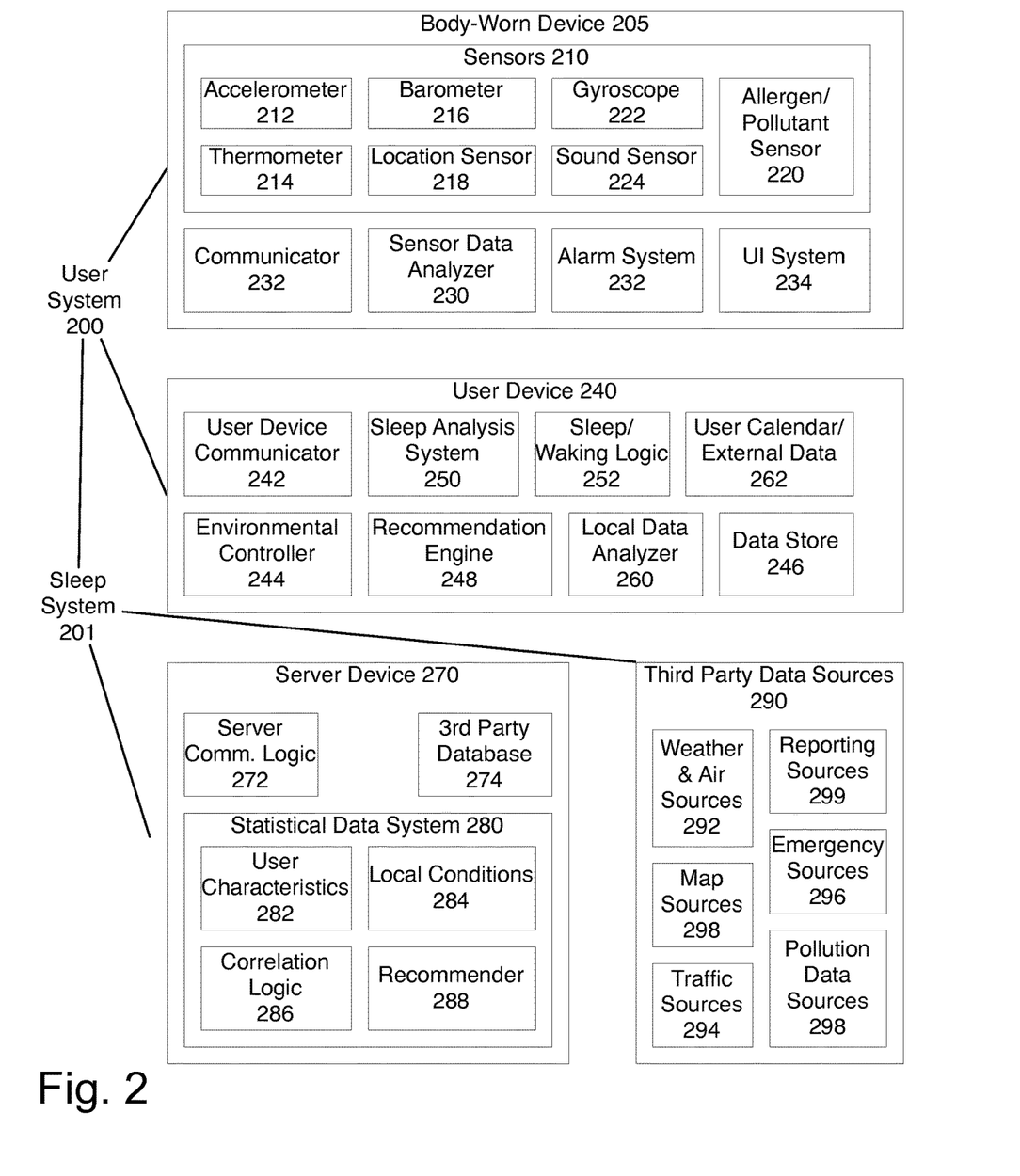
FIG. 2 is a block diagram of one embodiment of a sleep system.

FIG. 2 is a block diagram of one embodiment of a sleep system 201, which includes the user system 200, and optionally server device 270 and third party data sources 290. The user system 200 includes a plurality of sensors 210. These sensors 210 are on a body-worn device 205, in one embodiment, to sense the environmental and personal conditions of the user. In one embodiment, the body-worn device may be a wristband, a mobile device, a clip-on sensor system, or another type of device that is carried by the user or in sufficiently close proximity to the user to pick up the user's movements during sleep, and share the local environment with the user. The sensors 210 in one embodiment include an accelerometer 212 and/or gyroscope 222 to sense user movement, a barometer 216 and thermometer 214 to measure local weather conditions. In one embodiment, a humidity sensor may also be included as a sensor 210. Other environmental measurement sensors may also be included. Allergen/pollutant sensor 220 may be included, in one embodiment.

Additionally, sensors 210 may include a location sensor 218, such as a GPS, cellular network and/or wireless network-based location sensor. Other methods of determining the location of the body-worn device 205, and thus the user, may be utilized. In one embodiment, the user may enter the address directly. In one embodiment, location data may be received from a location application, outside the sleep system 200.

In one embodiment, a microphone or other sound sensor 224 may also be included. In one embodiment, light sensor may also be included, as may other sensors to measure the current conditions in the user's immediate vicinity. In one embodiment, one or more of these sensors 210 may be turned on periodically, as needed. Thus, in one embodiment, when the device detects that it is not being worn or used, the sensors may be turned off, except for the periodic testing by one sensor (such as accelerometer 212, gyroscope 222, location sensor 218, thermometer) to determine whether the device is worn or in use. In one embodiment, the sensor with the lowest power consumption that is capable of detecting use, is selected for such testing. In one embodiment, sensors that are unlikely to encounter rapid changes, such as allergen/pollutant sensor 220, or barometer 216, are periodically enabled, to obtain data, and are otherwise off to conserve power. In one embodiment, to save storage, the system does not store data that is unchanged, but simply uses an indicator for "no change." In one embodiment, the stored data may simply indicate the delta change, rather than store the full data set, as well. This reduces the required storage for sensor data on the body-worn device. In one embodiment, body-worn device 205 communicates with user device 240, using communicator 232. In another embodiment, the body-worn device 205 and user device 240 are integrated into a single device, such as a smart phone.

The analysis of the sensor data may be done by body-worn device 205, user device 240, or remote server 270, or a combination of the above. In one embodiment, sensor data analyzer 230 in body-worn device 205 performs a preliminary analysis, and sends pre-processed data to user device 240. The preliminary analysis may reduce the sensor data to a data subset. In one embodiment, the body-worn device 205 stores the original data, and provides the full data set to the user device 240 when the body-worn device 205 has a direct connection to the user device 240 (e.g. when the two are linked via a wired connection). In one embodiment, the pre-processed data is provided to user device 240 using a wireless connection.

The sleep analysis system 250 in user device 240 analyzes the user's sleep patterns, as well as how well the user is sleeping. In one embodiment, the user may, through UI system 234 of the body-worn device 205 or through a user interface in the user device 240 (not shown) add additional information about the quality of his or her sleep.

In another embodiment, the sleep analysis may be performed by server device 270, which may receive the data from body-worn device 205 and/or user device 240. In another embodiment, the sharing of processing may depend on the available battery levels of the devices. Other methods of distributing processing between the two local devices, body-worn device 205 and user device 240 and the server 260 may be used.

Sleep/waking logic 252 sets the timing for prompting the user to sleep, and/or waking the user. In one embodiment, based on local data, the system may recommend for example going to bed earlier, or sleeping until later. The sleep/waking logic 252 determines the optimal time for waking the user.

In one embodiment, the optimal time may be based on various local factors, user preferences, and/or user habits. For example, if the user is in the habit of running in the morning before work, the system may adjust the waking time when a particularly hot day is expected, so that the user can complete his or her run before the temperatures become too high. Similarly, if there is rain, and the user does not run in the rain, the user's alarm may be adjusted since there is no need to have time for a run. In one embodiment, alarm system 232 is used to wake the user. Alarm system may be on body-worn device or user device, or both.

User calendar/external data logic 262 accesses external data that may influence the user's sleep. This external data is not local condition data, but rather data such as information on the user's calendar, contacts, habits, or other relevant data available to the system, that may influence when the user should go to sleep or wake up.

Environmental controller 244, in one embodiment, controls the user environment when that is possible. With increasing home automation, more and more home environments may be controlled using a mobile device, such as a smart phone. For example, there are controls available for heating/cooling, humidity, opening and closing curtains or turning on and off other light sources, etc. In one embodiment, the environmental controller 244 may adjust any user device controllable environmental variables, to support the user's sleep. Recommendation engine 248 recommends other changes to the user, e.g. to make environmental changes that cannot be controlled by environmental controller 244. Such changes may include opening or closing windows, opening or closing non-automated curtains, turning on and off heaters/air conditioners/dehumidifiers/humidifiers, turning off loud devices, etc.

These recommendations are based on the local data and the sleep data. The local data is obtained from third party data sources 290, or third party database 274 maintained by a server 270. Local data analyzer 260 in user device 240, in one embodiment, analyzes the local data. In one embodiment, recommendation engine 248 also receives data from statistical data system 280.

In one embodiment, statistical data system 280 collects data from many users, and creates correlations and recommendations, based on a combination of the available user's characteristics 282 (e.g. age, gender, health conditions, etc.), local conditions 284 (e.g. pollution levels, noise levels, etc.), and data from many user's as identified by correlation logic 286. In one embodiment, users may opt out of being part of the statistical system.

Recommender 288 abstracts the correlated data from statistical system 280 to enable refining of recommendations sent to recommendation engine 248. For example, the recommender 288 may identify an age range and health condition set for which a particular recommendation is applicable. Furthermore, in on embodiment local conditions 284 may be abstracted, so rather than saying "in Santa Cruz, next to Highway 1" the local condition may be "near the ocean, 0.25 miles from freeway." In one embodiment, the abstraction of the local conditions may be based on the condition type. For example, for allergen count, the abstracted location may be a distance (e.g. within 10 miles of a eucalyptus forest, or within 5 miles of allergen station X), altitude, or other relevant characteristic. This abstracted local condition is more useful to match the data to other users.

Third party data sources 290 may include weather & air condition sources 292, map sources 298, traffic sources 294, emergency reporting sources 296, reporting sources 299, and pollution data sources 298. In one embodiment, the local data analyzer 260 obtains data for the location, and then updates the data periodically. In one embodiment, when the user has previously been at the location, only changed data is obtained from the third party data sources. In one embodiment, relatively static data may be refreshed periodically as well. In one embodiment relatively static data such as map locations, pollution sources, traffic levels may be updated only periodically, whereas highly fluctuating data such as allergen load, current weather, and emergency status is updated more frequently.

In this way, the sleep system 200 which may include separate body-worn device 205 and user device 240, or a combined device that includes processing capabilities and sensors, provides local data modulated sleep recommendations to the user.

For simplicity, the blocks representing the various sensors and processing logics are not reproduced in each of the devices. However, one of skill in the art would understand that the logic may be present in one or more of the devices, and that each of the devices in the sleep system 201 may perform any of the processing described.

In one embodiment, the body-worn device 205 may implement the processing logics described in a low power processor, such as an ARM CORTEX processor. The user device 240 may be a smart phone or similar device, and may in one embodiment implement the processing logics using a dual-processor implementation, in which a lower powered real-time processor is supplemented by a higher power processor, for more complex calculations. The server 260 may have multiple processors, or may be a cloud-based computer implementation that utilized distributed processing, rather than a dedicated processor.

It would be obvious to one of ordinary skill in the art that while the description here focuses on sleep, a logical extension would be to provide local data mediated activity recommendations. For example, the user may be recommended in-door exercise for days that are high in relevant allergens or pollution, or when the temperature or humidity is too high. The user may be recommended out-door exercise for a sunny and pleasant day. The user may be recommended exercise earlier or later in the day, depending on local conditions. Other recommendations may follow logically from the sleep data described, e.g. food recommendations, exercise recommendations, activity recommendations, etc.

Figure 3:
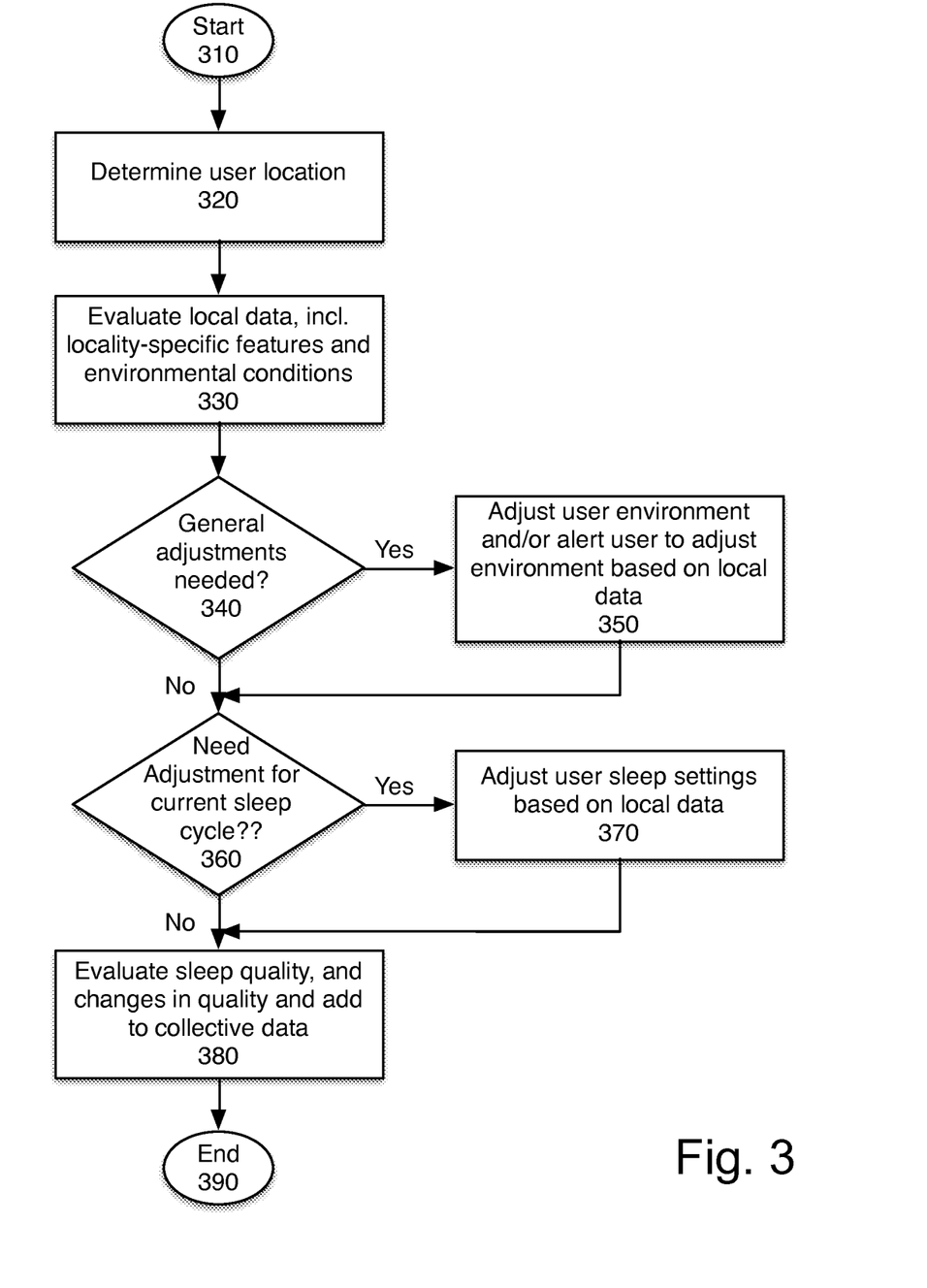
FIG. 3 is an overview flowchart of one embodiment of using local data to improve sleep experience.

FIG. 3 is an overview flowchart of one embodiment of using local data to improve sleep experience. The process starts at block 310.

At block 320, the process determines the user's location. Although time zone can be used as a proxy for location, having an actual location is more useful. In one embodiment, the user device may include a global positioning system (GPS) chip, which may determine the user device's location. In one embodiment, location may be determined based on network triangulation, using a cellular network. In one embodiment, a wireless network-based location determination is used.

At block 330, the system evaluates local data, including locality specific features and environmental conditions. Local data has two aspects, permanent local data and temporary local data, also referred to as locality specific data and local conditions, respectively.

Figure 7:
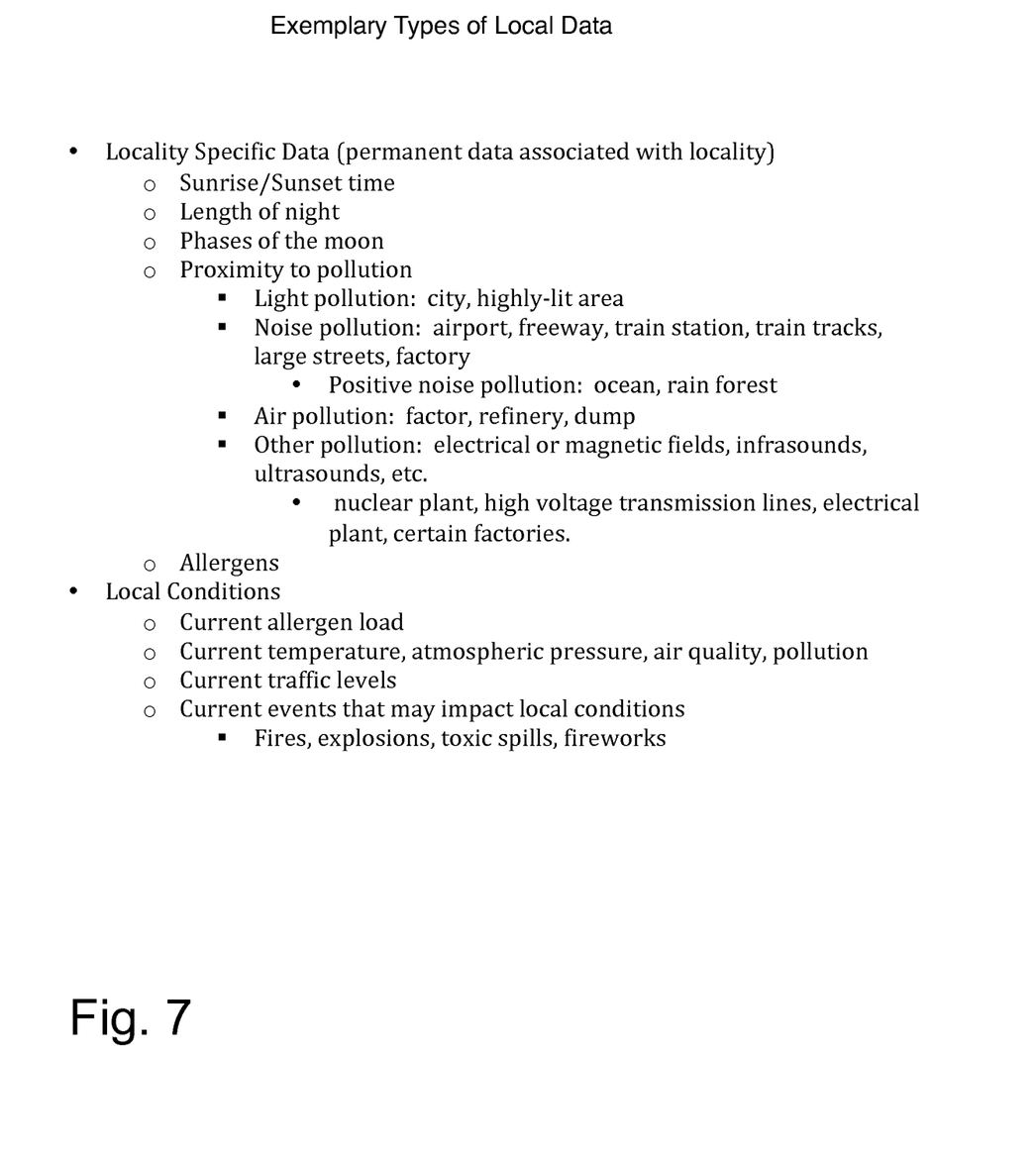
FIG. 7 is a chart of some exemplary types of local data.

FIG. 7 illustrates some exemplary local information. The exemplary locality specific data include information about local features, such as local factories, freeways, airports, etc. Locality specific data may also include the local sunrise/sunset times, length of night, and phase and appearance of the moon. In one embodiment, general pollution, light pollution, noise pollution, air pollution, electrical/magnetic field pollution, and other types of locality specific data are also included in the local data.

In one embodiment, locality specific data may include the types of allergens present locally. This may be based on air quality sampling, and indicates the types of plants, pollutants, and other known allergens that are locally present. Like moon phases, although the general allergens change seasonally, the local plant types do not change frequently. Therefore, allergen types may be classified, in one embodiment, as locality specific data.

In one embodiment, locality specific data is any data that does not change rapidly, and thus does not need to be-revalidated frequently. For example, although sunrise/sunset times change through the months, the pattern is defined by the latitude & longitude, and once that is determined, it need not be re-evaluated. While certain aspects may change over time, e.g. a new freeway may open, a factory may close, these changes are rare. Thus, while locality specific data may be periodically re-validated, it need not be checked often.

In contrast, current local conditions, which are also considered local data, are the temporary features associated with the locality. These features include current allergen load, current temperature, atmospheric pressure, air quality. The local conditions also may include current traffic levels. In one embodiment, current events that may impact local conditions, such as nearby fires, explosions, toxic spills, fireworks, or other noisy activities may also be included in the data set of local data.

Returning now to FIG. 3, at block 340 the process determines whether changes need to be made to the user's environment, based on the local data, and the user information. If so, at block 350, the user environment is adjusted. In one embodiment, some settings may be automatically changed. In one embodiment, for some changes that cannot be automatically controlled by the system, the user may be alerted to make changes. An exemplary automatic adjustment may be to turn on a white noise, to counter noise pollution at the user's location. An exemplary user alert may be to ask the user to turn on a HEPA filter, if the air pollution levels indicate that this would likely increase the user's sleep quality. The process then continues to block 360. If no changes are needed, the process continues directly to block 360.

At block 360, the process determines whether the system needs to make adjustments for a current sleep cycle. In one embodiment, this step is only taken if the user is currently asleep. The current sleep cycle adjustments may include shifting the waking time for the user, changing the user's environment to support the user's current sleep cycle, or to shift the user to a more appropriate sleep cycle. In one embodiment, the adjustments may also include other changes. The process then continues to block 380.

At the end of the sleep period, at block 380, the system evaluates the sleep quality of the user. In one embodiment, this may be based on the user sleep data, as detected by the sensors. In one embodiment, the user may also add information about his or her sleep quality. For example, in one embodiment, when the alarm sounds, the screen presented to the user enables the user to rate his or her sleep quality. In one embodiment, the sleep quality may be rated on length, restfulness, and comfort. In another embodiment, the user rates his or her overall mood, and that is added to the automatically determined information, calculated based on movement during sleep, time in each sleep phase, and length of sleep.

In one embodiment, the user sleep quality is correlated with the location data, and past sleep data for the user. In one embodiment, the user's data is also added to the cumulative data, if the user's privacy settings permit such data collection. In one embodiment, the user may control how his or her sleep data and local data is used. The process then ends at block 390.

In one embodiment, the system continues to monitor local conditions. In one embodiment, in addition to utilizing local condition data for sleep, the system may also utilize this local condition data for other purposes. The user's environment may also be adjusted, and/or the user alerted, based on local condition data and locality specific data, for non-sleep periods. For example, if the user has scheduled bicycling, but the air pollution index is above a certain level, the system may alert the user that an alternative form of exercise may be preferred. For example, the user may be provided an alarm prior to a meeting, that is adjusted based on local temperature and traffic levels. Other uses for local condition data would be understood by one of skill in the art.

Figure 4:
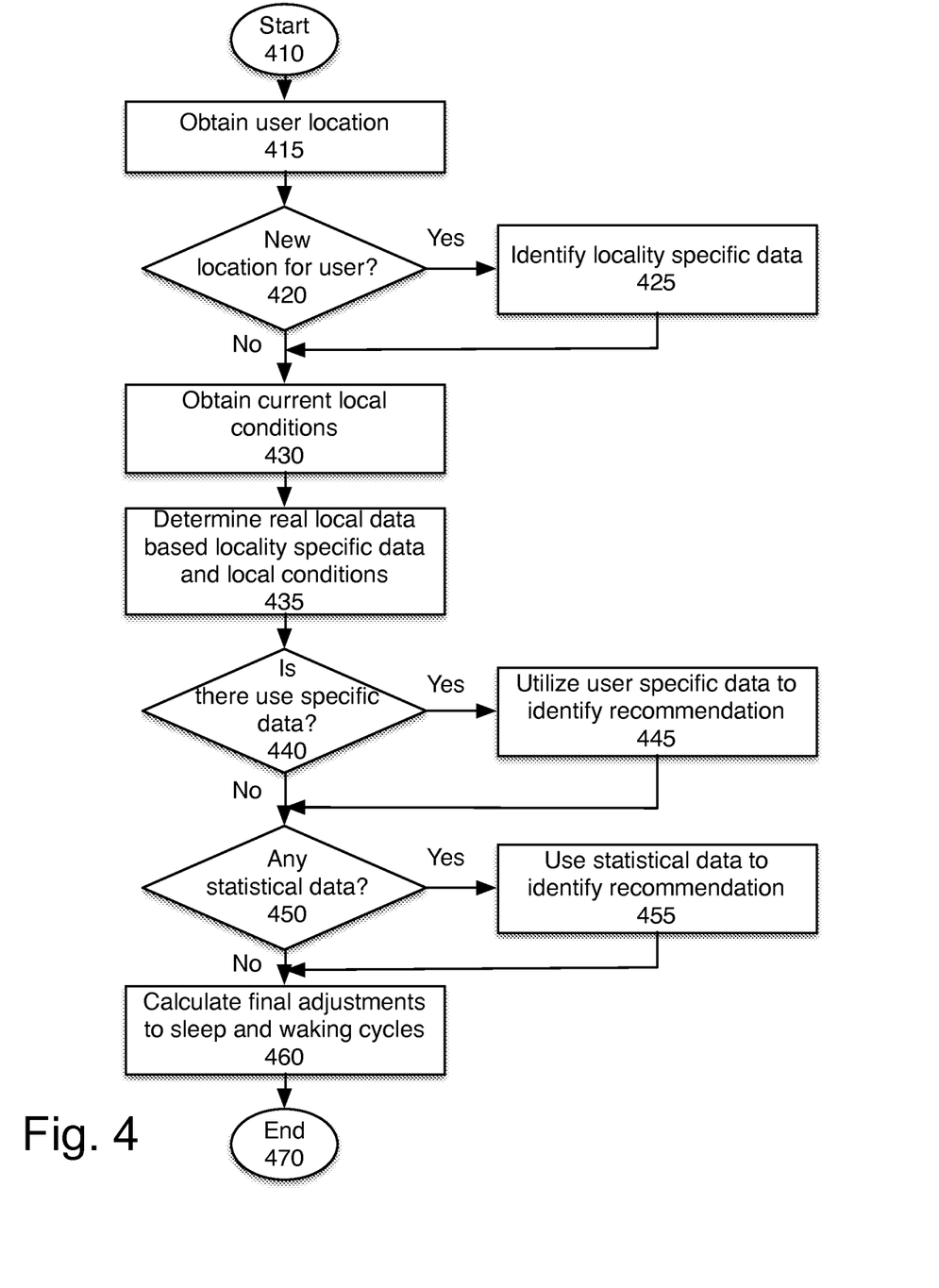
FIG. 4 is a flowchart of one embodiment of changing settings.

FIG. 4 is a flowchart of one embodiment of changing settings. This process, in one embodiment, is implemented when the timing indicates that the user is likely to be going to bed shortly. In one embodiment, this may be based on an alarm and the user's usual sleep period. For example, if the user has set a 6 am alarm, and the user generally sleeps for 8 hours, this process may be initiated at 30 minutes before the proposed bedtime of 10 pm. In one embodiment, this may be based on the usual time when the user goes to sleep. In one embodiment, this may be based on data from the user's body-worn device, which is identified as an activity taken in preparation for sleep, such as going into the bedroom, brushing teeth, changing into sleepwear, etc.

The process starts at block 410. At block 415, the process obtains the user's location. In one embodiment, the user location may be received from a GPS chip or an application that does location processing. In another embodiment, the system may calculate the user's location based on cellular network data, wireless network data, or GPS data.

At block 420, the process determines whether this is a new location for the user. If so, at block 425, the system retrieves the locality specific data for the new location. In one embodiment, even if this is not a new location, the system periodically retrieves locality specific data to ensure no changes have taken place. In one embodiment, the period for locality specific data retrieval may vary by data type. For example, for local highways and moon phases, the system need not update more frequently than every 6 months, whereas for allergen types, light pollution, or electric/magnetic fields, the system may update on a monthly, weekly, or even daily basis. Other intervals for such updates may be selected by the system, or customized by the user. In one embodiment, the user may trigger an update for locality specific data.

At block 430, the process obtains current local conditions. In one embodiment, this is retrieved from a server, or from one or more remote data sources. In one embodiment, the remote data sources are obtained from the server, for a new location. In one embodiment, the server includes a plurality of third party sources that have relevant information for a particular locality. Thus in one embodiment, the system retrieves the data source information from the server, and then retrieves the local data from the identified third party sources.

At block 435, the real local data is determined. The local data is determined based on the combination of the locality specific data and current local conditions. In some cases, locality specific data may be overridden by current local conditions. For example, local noise levels dictated by locality specific data may be overridden by the current local conditions.

At block 440, the process determines whether there is user-specific data that may be used to identify a recommendation for the user. In one embodiment, the recommendation is based on the user's own past reactions to local data. For example, the system may have determined that the user is allergic to pine pollen, and the local data may indicate that the current local load of pine pollen is high.

At block 445, the user specific data is used to identify a recommendation. Note that while the specific locality may be different, reactions to a similar set of conditions (for example, similar length of night, noise level, and pollution level) may be used to generate a user-specific data set, for a recommendation.

In one embodiment, the recommendation may further be based on statistical data from other users in similar circumstances and with similar local conditions. In one embodiment, the circumstances may be user attributes. In one embodiment, user attributes may be health conditions, such as asthma, diabetes, or temporary health conditions such as allergies or broken bones. In one embodiment, user attributes may be characteristics such as age, overall aerobic condition, etc. A user with asthma, or diabetes, or an athlete may each have different reactions to local circumstances. For example, the system may find that users that are highly athletic, when sleeping at a higher elevation need to have higher humidity/cooler temperature. For example, the system may find that someone with allergies sleeps better in a higher humidity environment. Similarly, factors based on local conditions (e.g. proximity to coal fired plant, proximity to ocean, or even local insect or bird populations, may impact a user's sleep experience. Specific correlations may be found, based on analyzing large statistical data sets.

At block 450, the process determines whether there is any statistical data that may be used to identify a recommendation. In one embodiment, if a user shares his or her data, the system makes available data from other users who have chosen to share. In such a case, the system determines whether there are other users who have provided their information, associated with similar local data.

If so, at block 455, the statistical data is used to identify a recommendation. For example, the system may have determined that when there is smoke in the air, people need to sleep longer to get an equal quality of rest. If the local data indicates that there is a plume of smoke from a forest fire, this may be used to identify a recommendation to shift the user's sleep schedule or adjust other environmental factors At block 460, the system provides final adjustments. These adjustments may include changes to the sleeping environment or waking, implemented by the user or automatically by the system. These adjustments in one embodiment include changes to a user wake time. These adjustments may include recommendations to the user. In one embodiment, these changes may include how a user is woken up. For example, when it's a bright, sunny day with good air quality, the waking cycle may be initiated by opening the shades and possibly the windows to let in light, fresh air and sounds of birds chirping to wake up the user naturally. Whereas on a cloudy dark overcast morning, or a day with poor air quality, the system may use artificial lighting and/or sounds/vibrations to wake up the user. The process then ends, at block 470.

Figure 5:
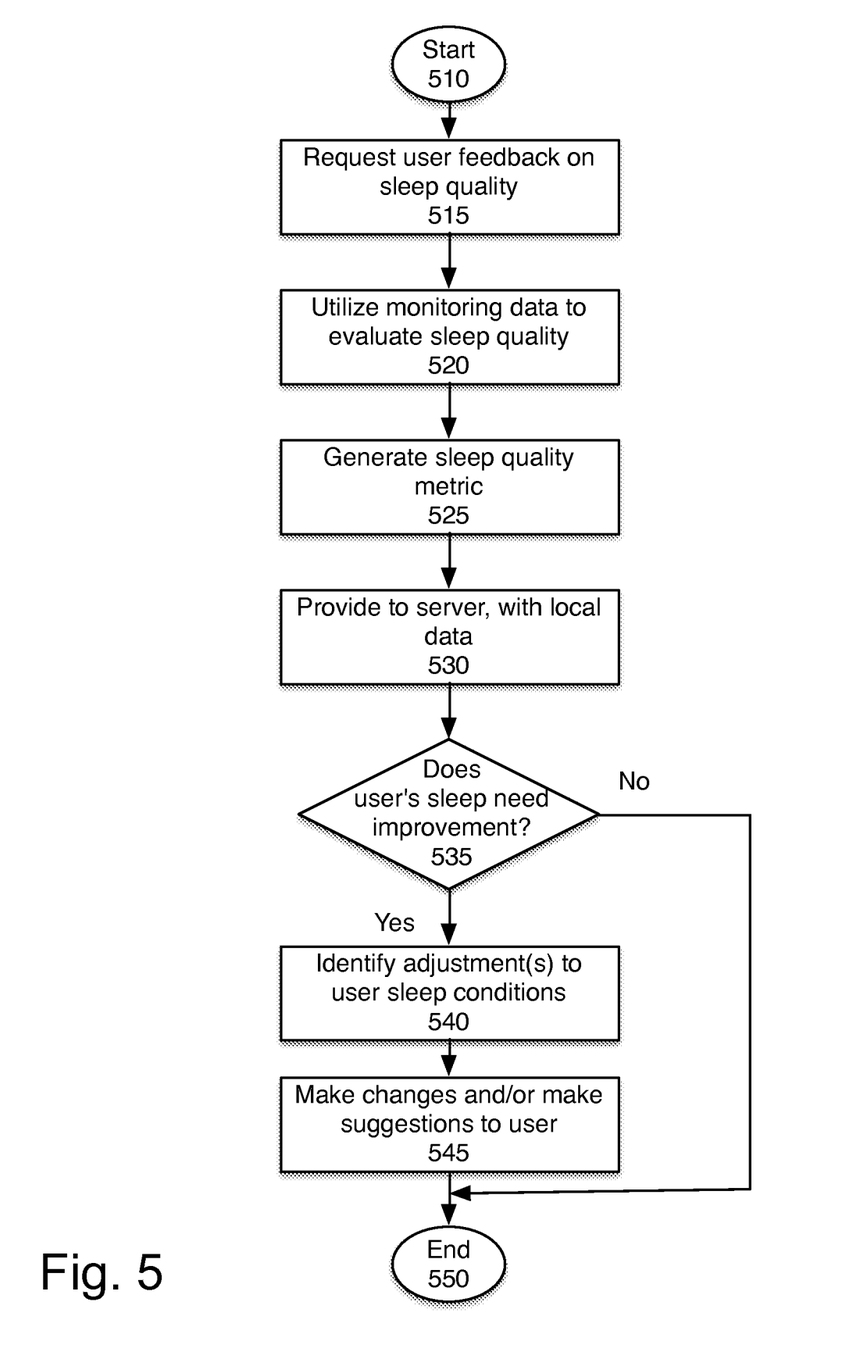
FIG. 5 is a flowchart of one embodiment of the evaluation and feedback system.

FIG. 5 is a flowchart of one embodiment of the evaluation and feedback system. The process starts at block 510. At block 515, the process requests user feedback on sleep quality. In one embodiment, upon waking the user may indicate his or her sleep quality for the night. In one embodiment, the sleep quality indication may be a simple numeric evaluation. For example, the evaluation may provide a scale of 1 to 10, with 1 being the worst and 10 being the best, and the user can indicate a score, e.g. 6 out of 10. In one embodiment, the evaluation may include ratings along multiple axes (e.g. restfulness, refreshment, mood, dreams). In one embodiment the feedback is requested when the user initially wakes up. In one embodiment, follow-up feedback is requested later in the day, so the user can provide additional information about how alert, competent, and awake they felt during the day. In one embodiment, providing this feedback is optional.

At block 520, the system uses the monitoring data to evaluate the sleep quality automatically. The user's movements during sleep, the percentage of deep sleep, REM (rapid eye movement) sleep, and other factors may be taken into account when evaluating sleep quality. In one embodiment, if the automatic evaluation and the user's input differs, the user's input controls the determination. In one embodiment, if such differences are statistically significant, the automatic sleep quality evaluation is adjusted to more closely parallel the predicted quality as perceived by the user. In one embodiment, if there is a significant difference between the user's perceived quality of sleep and the restfulness of the sleep as evaluated by the system automatically, the system alerts the user to this discrepancy. Such errors in perception of restfulness may be an indicator of sleep issues.

At block 525, in one embodiment, the system generates an overall sleep quality metric. This may be a single rating, or a more complex evaluation, as noted above.

At block 530, in one embodiment, the local data and the sleep quality metric is provided to the computing device. In one embodiment, that computing device is a server, however the computing device may alternatively be the user's personal computer or mobile computer, such as a smart phone. In one embodiment, if the user's data is uploaded to a server, the data may be added to the cumulative statistical data for all users, if the user authorizes it to be shared.

At block 535, the process determines whether the user's sleep quality needs improvement. In one embodiment, this determination is made based on the user's self-assessed sleep quality, automatically determined sleep quality, and baseline healthy sleep data for the user's demographic. For example, an adolescent user may self-rate sleeping 4 hours a night as being sufficient. However, studies show that less than 7 hours of sleep a night is unhealthy, especially for an adolescent. Therefore, this determination may be based on scientific data, as well as self-reported or detected data. If no improvement is needed, the process ends at block 550.

If the user's sleep quality needs improvement, at block 540, the system identifies adjustments to the user's sleep conditions that may improve sleep quality. As noted above, this may be based on data from the specific user, statistical data from many users, and/or research data.

At block 545, if any of the changes can be made automatically, they are made, in one embodiment. In one embodiment, appropriate recommendations are made to the user. For example, the system may find that if the user goes to sleep after 1 a.m., the sleep quality suffers. Or the system may determine that if the user wakes before full daylight, their sleep quality suffers. Or the system may determine that if the noise level is above a threshold, the user's sleep quality suffers. The system may automatically prompt the user to go to bed earlier, change the alarm time, or enable a white noise machine, in the examples above.

In one embodiment, if there is no other change that can be made, and the impact on the user's sleep quality is severe; the system may recommend that the user leave the local area. The process then ends at block 550.

Figure 6:
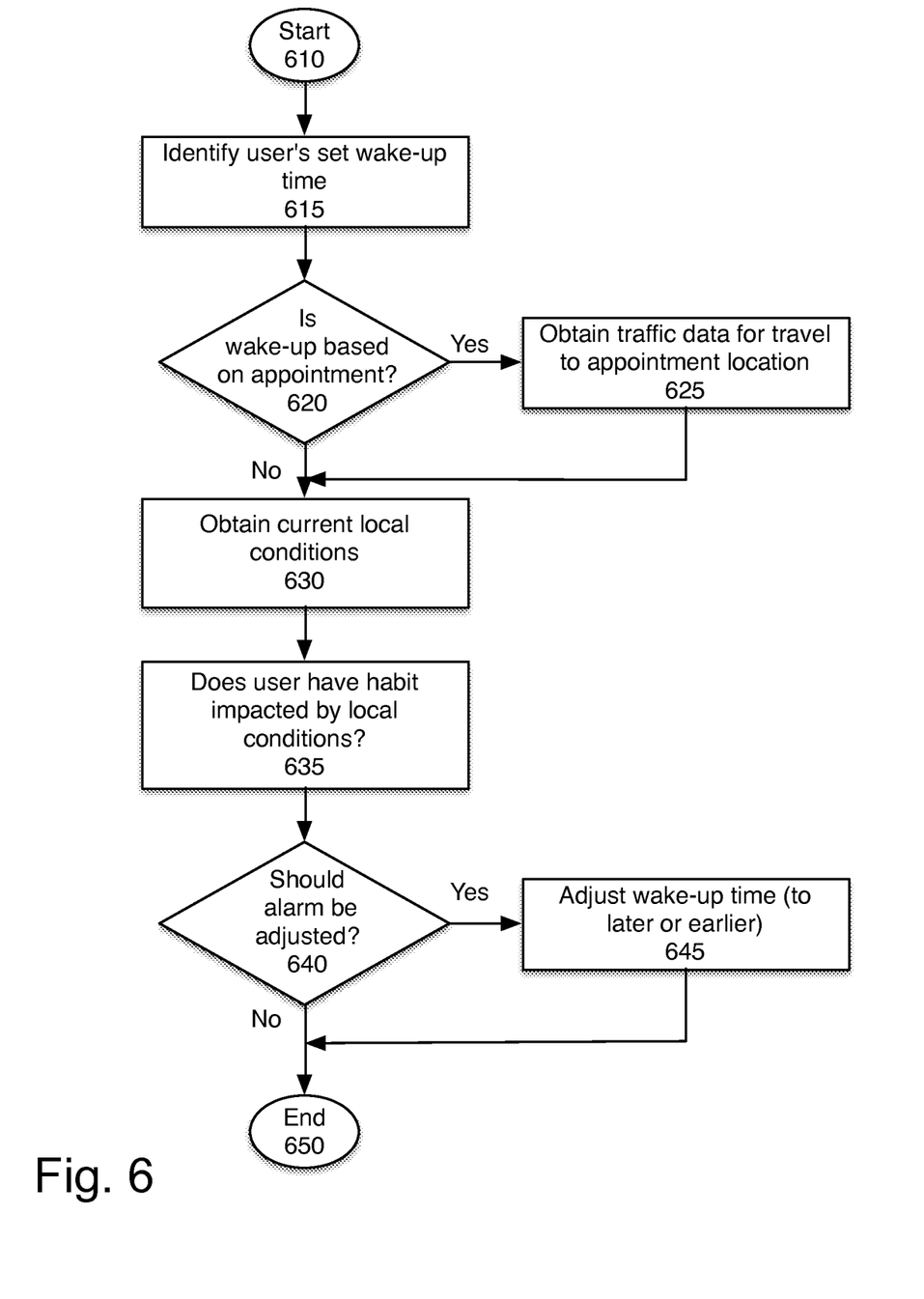
FIG. 6 is a flowchart of one embodiment of alarm adjustment, based on local data.

FIG. 6 is a flowchart of one embodiment of alarm adjustment, based on local data. The process starts at block 610. In one embodiment, this process is initiated when the user falls asleep. In one embodiment, this process is initiated prior to the user's set wake-up time, but sufficiently near the time to have accurate current local condition data.

At block 615, the user's set wake-up time is identified. In one embodiment, wake-up time may be based on a variety of factors, including alarms set by the user, appointments on the user's calendar, the user's stated preference for length of sleep periods. In one embodiment, if there is no preferred wake-up time, e.g. the user has not expressed a preference and there is no external data that would provide a wake-up time, the process ends. In one embodiment, if there is no preferred wake-up time, the system sets a wake-up time based on historical data for the user. In one embodiment, in addition to the average length of sleep, the system may also take into account the day of the week, and the user's standard schedule. For example, a user may sleep 7 hours on weekdays but generally sleep 9 hours on the weekend. The preferred wake-up time would be set based on whether the date is a weekday or weekend. Note that in this context, Friday night is a weekend, while Sunday night is a weekday, since the waking up occurs during a weekday morning.

The process determines whether the wake-up time is based on an appointment, at block 620. In one embodiment, the system interacts with the user's calendar to make this determination. In one embodiment, the calendar may be on the user's device. In one embodiment, the mobile device includes both the local data analysis and the calendar data, and the user may set to share the calendar data with the sleep analysis system.

If the wake-up is based on an appointment, in one embodiment, at block 625, traffic data for travel to the location of the appointment is obtained. In one embodiment, the traffic data may be current actual traffic data near the wake-up time, or prospective traffic data if this evaluation is done earlier.

At block 630, the current local conditions are obtained.

At block 635, the process determines whether the user has a habit impacted by local conditions, or something scheduled that may be impacted by the local data. Habits may include morning exercise, bicycling to work, hiking on Sunday mornings, etc. Any outdoor activity that the user regularly takes, is relevant to the current wake-up setting, would be considered a relevant habit.

At block 640, the process determines whether the alarm should be adjusted, based on the user's appointments or expected actions, and local data. If so, at block 645, the adjustment is made. In one embodiment, if the user's set wake-up time for an appointment is too short given actual traffic conditions, the wake-up time should be shifted. If the user cannot take the outdoor activity (e.g. biking to work) due to the local conditions, such as a smog alert, the wake-up time may be adjusted to later. If the user's planned activity has a particular timeframe associated with it (e.g., a morning hike would be better on a day that is likely to be very hot), the wake-up time may be appropriately adjusted. The process then ends. In one embodiment, the system continues to monitor local conditions until the user is woken up, and subsequent adjustments may be made.

Figure 8:
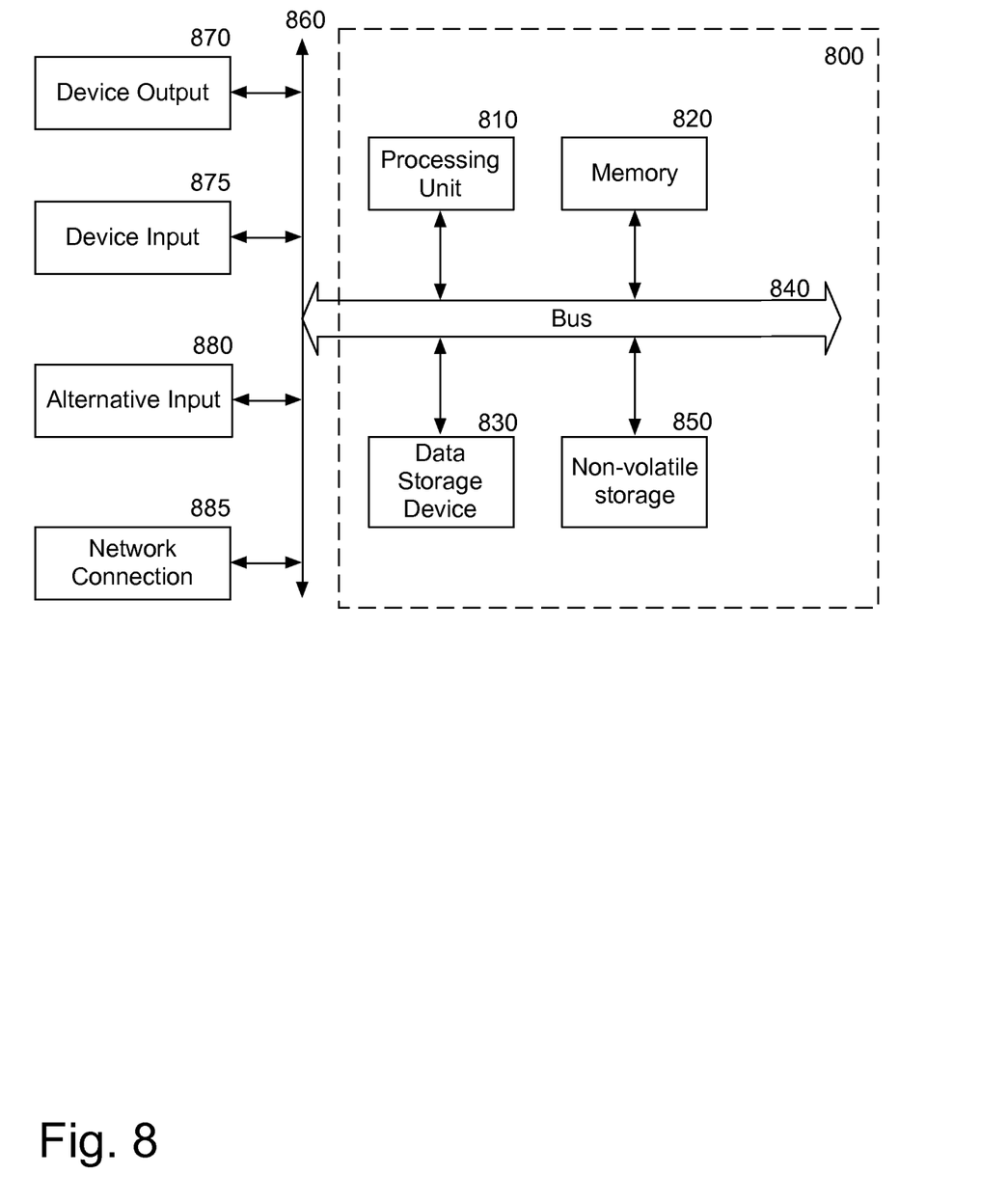
FIG. 8 is a block diagram of one embodiment of a computer system that may be used with the present invention.

FIG. 8 is a block diagram of one embodiment of a computer system that may be used with the present invention. It will be apparent to those of ordinary skill in the art, however that other alternative systems of various system architectures may also be used.

The data processing system illustrated in FIG. 8 includes a bus or other internal communication means 840 for communicating information, and a processing unit 810 coupled to the bus 840 for processing information. The processing unit 810 may be a central processing unit (CPU), a digital signal processor (DSP), or another type of processing unit 810.

The system further includes, in one embodiment, a random access memory (RAM) or other volatile storage device 820 (referred to as memory), coupled to bus 840 for storing information and instructions to be executed by processor 810. Main memory 820 may also be used for storing temporary variables or other intermediate information during execution of instructions by processing unit 810.

The system also comprises in one embodiment a read only memory (ROM) 850 and/or static storage device 850 coupled to bus 840 for storing static information and instructions for processor 810. In one embodiment, the system also includes a data storage device 830 such as a magnetic disk or optical disk and its corresponding disk drive, or Flash memory or other storage which is capable of storing data when no power is supplied to the system. Data storage device 830 in one embodiment is coupled to bus 840 for storing information and instructions.

The system may further be coupled to an output device 870, such as a cathode ray tube (CRT) or a liquid crystal display (LCD) coupled to bus 840 through bus 860 for outputting information. The output device 870 may be a visual output device, an audio output device, and/or tactile output device (e.g. vibrations, etc.)

An input device 875 may be coupled to the bus 860. The input device 875 may be an alphanumeric input device, such as a keyboard including alphanumeric and other keys, for enabling a user to communicate information and command selections to processing unit 810. An additional user input device 880 may further be included. One such user input device 880 is cursor control device 880, such as a mouse, a trackball, stylus, cursor direction keys, or touch screen, may be coupled to bus 840 through bus 860 for communicating direction information and command selections to processing unit 810, and for controlling movement on display device 870.

Another device, which may optionally be coupled to computer system 800, is a network device 885 for accessing other nodes of a distributed system via a network. The communication device 885 may include any of a number of commercially available networking peripheral devices such as those used for coupling to an Ethernet, token ring, Internet, or wide area network, personal area network, wireless network or other method of accessing other devices. The communication device 885 may further be a null-modem connection, or any other mechanism that provides connectivity between the computer system 800 and the outside world.

Note that any or all of the components of this system illustrated in FIG. 8 and associated hardware may be used in various embodiments of the present invention.

It will be appreciated by those of ordinary skill in the art that the particular machine that embodies the present invention may be configured in various ways according to the particular implementation. The control logic or software implementing the present invention can be stored in main memory 820, mass storage device 830, or other storage medium locally or remotely accessible to processor 810.

It will be apparent to those of ordinary skill in the art that the system, method, and process described herein can be implemented as software stored in main memory 820 or read only memory 850 and executed by processor 810. This control logic or software may also be resident on an article of manufacture comprising a computer readable medium having computer readable program code embodied therein and being readable by the mass storage device 830 and for causing the processor 810 to operate in accordance with the methods and teachings herein.

The present invention may also be embodied in a handheld or portable device containing a subset of the computer hardware components described above. For example, the handheld device may be configured to contain only the bus 840, the processor 810, and memory 850 and/or 820.

The handheld device may be configured to include a set of buttons or input signaling components with which a user may select from a set of available options. These could be considered input device #1 875 or input device #2 880. The handheld device may also be configured to include an output device 870 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above, such as a kiosk or a vehicle. For example, the appliance may include a processing unit 810, a data storage device 830, a bus 840, and memory 820, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 885.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 810. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A method performed by a device to improve a user's sleep, comprising:
    identifying a user location and storing the user location in memory of the device;
    automatically obtaining, via a computer network, local data from a third party database, the obtained local data comprising local pollution data having a location and a pollution type of one or more external pollution sources and the obtained local data further comprising highly fluctuating local data, wherein the local pollution data is obtained from the database periodically, and wherein the highly fluctuating local data is obtained from the database more frequently than the local pollution data;
    determining proximity of the user location to the one or more external pollution sources;
    acquiring additional local data relevant to the user's sleep quality utilizing one or more sensors;
    evaluating a sleep environment of the user and sleep settings based on the local data from the third party database, the determined proximity of the user location to the one or more external pollution sources, and the additional local data from the one or more sensors during a sleep session; and
    automatically changing the user's sleep environment or sleep settings based on the evaluation to improve the user's sleep quality.

2. The method of claim 1, wherein the local data from the third party database includes locality specific data and current local conditions.

3. The method of claim 2, wherein the locality specific data includes one or more of: sunrise/sunset time, length of night, and phases of the moon.

4. The method of claim 2, wherein the current local conditions include one or more of: allergen load, air quality, traffic levels, fires, and toxic spills.

5. The method of claim 1, wherein the proximity to the one or more external pollution sources comprises proximity to one or more of: external light pollution, noise pollution, air pollution, electrical or magnetic field pollution, and infrasound pollution.

6. The method of claim 1, wherein changing the user's sleep environment or sleep settings comprise one of: adding white noise, removing sounds, changing a waking time, adjusting light levels, adjusting temperature, and altering waking conditions.

7. The method of claim 1, wherein changing the user's sleep environment comprises one or more of: utilizing an air filter, changing a room temperature, and closing curtains.

8. The method of claim 1, further comprising:
    alerting a user to change the user's sleep environment for subsequent sleep sessions by one of: utilizing an air filter, changing a room temperature, closing curtains, using earplugs, turning on a white noise machine, and adjusting light levels.

9. The method of claim 1, wherein the sensors comprise one or more of: a barometer, a thermometer, a sound sensor, a location sensor, and an accelerometer.

10. The method of claim 9, wherein the sensor comprises a location sensor, and wherein data from the location sensor is used to obtain locality specific data.

11. An apparatus, comprising:
    a location sensor to determine a user location;
    a processor connected to a network connection configured to obtain local data from a third party database, the obtained local data comprising local pollution data having location and pollution type of one or more external pollution sources and, the obtained local data further comprising highly fluctuating local data, wherein the local pollution data is obtained by the processor from the database periodically, and wherein the highly fluctuating local data is obtained by the processor from the database more frequently than the local pollution data;
    one or more sensors acquiring additional local data relevant to a user's sleep quality;
    the processor further configured to use the local data from the third party database to determine a proximity of the user location to the one or more external pollution sources;
    the processor further configured to continuously evaluate a user's sleep environment and sleep settings based on the local data from the third party database, the determined proximity of the user location to the one or more external pollution sources, and the additional local data during a sleep session; and
    a controller configured to automatically change the user's sleep environment or sleep settings based on the continuous evaluation to improve the user's sleep quality.

12. The apparatus of claim 11, wherein the local data from the third party database includes locality specific data and current local conditions.

13. The apparatus of claim 12, wherein the locality specific data includes one or more of: sunrise/sunset time, length of night, and phases of the moon.

14. The apparatus of claim 12, wherein the current local conditions include one or more of: allergen load, temperature, atmospheric pressure, air quality, pollution levels, traffic levels, fires, toxic spills.

15. The apparatus of claim 11, wherein the proximity to the one or more external pollution sources comprises proximity to: external light pollution, noise pollution, air pollution, electrical or magnetic field pollution, infrasound pollution.

16. The apparatus of claim 11, wherein changing the user's sleep environment or sleep settings comprise one of: adding white noise, removing sounds, changing a waking time, adjusting light levels, adjusting temperature, and altering waking conditions.

17. The apparatus of claim 11, wherein changing the user's sleep environment comprises one or more of: utilizing an air filter, changing a room temperature, and closing curtains.

18. The apparatus of claim 11, further comprising:
a user interface to alert a user to change the user's sleep environment for subsequent sleep sessions by one of: utilizing an air filter, changing a room temperature, closing curtains, using earplugs, turning on a white noise machine, and adjusting light levels.

19. The apparatus of claim 11, wherein the sensors comprise one or more of: a barometer, a thermometer, a sound sensor, a location sensor, and an accelerometer.

20. The apparatus of claim 11, wherein at least one sensor is in a body-worn device.

21. A method performed by a device to improve a user's sleep, comprising:
identifying a user location and storing the user location in memory of the device;
automatically obtaining, via a computer network, local data from a third party database, the obtained local data comprising local pollution data having a location and a pollution type of one or more external pollution sources and, the obtained local data further comprising highly fluctuating local data, wherein the local pollution data is obtained from the database periodically, and wherein the highly fluctuating local data is obtained from the database more frequently than the local pollution data;
determining proximity of the user location to the one or more external pollution sources;
acquiring additional local data relevant to the user's sleep quality utilizing one or more sensors;
continuously evaluating a sleep environment of the user and sleep settings based on the local data from the third party database, the determined proximity of the user location to the one or more external pollution sources, and the additional local data from the one or more sensors during a sleep session; and
automatically changing the user's sleep environment or sleep settings based on the continuous evaluation to improve the user's sleep quality, wherein changing the user's sleep environment or sleep settings comprise one of: adding white noise, removing sounds, changing a waking time, adjusting light levels, adjusting temperature, and altering waking conditions.

\* \* \* \* \*